US00PP33348P2

(12) United States Plant Patent
Olesen

(10) Patent No.: US PP33,348 P2
(45) Date of Patent: Aug. 17, 2021

(54) CLIMBING ROSE PLANT NAMED 'POULCY036'

(50) Latin Name: *Rosa hybrida*
Varietal Denomination: Poulcy036

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 16/873,999

(22) Filed: Sep. 3, 2020

(51) Int. Cl.
*A01H 5/02* (2018.01)
*A01H 6/74* (2018.01)

(52) U.S. Cl.
USPC ..... Plt./111

(58) Field of Classification Search
USPC ..... Plt./101, 109, 111
See application file for complete search history.

*Primary Examiner* — Susan McCormick Ewoldt

(57) ABSTRACT

A new garden rose plant of the Climbing class which has abundant, yellow flowers and attractive foliage. This new and distinct variety has shown to be uniform and stable in the resulting generations from asexual propagation.

2 Drawing Sheets

Botanical designation: *Rosa hybrida.*
Variety denomination: 'Poulcy036'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2002 and the resulting seeds were planted in a controlled environment in Fredensborg, Denmark. The new variety, named 'Poulcy036', originated as a single seedling from the stated cross.

The new variety may be distinguished from its male pollen parent and female seed parent primarily by the following characteristics. The male pollen parent plant has apricot yellow blend flowers while the new variety has pure yellow flowers. The female seed parent plant has small yellow flowers, about 30 to 35 mm in diameter, whereas the new variety has yellow flowers about 55 mm in diameter.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy036' from all other varieties of which we are aware.

As part of the rose development program, Mogens N. Olesen germinated the seeds from the aforementioned hybridization during winter of 2002 and conducted evaluations on the resulting seedlings in a controlled environment in Fredensborg, Denmark. 'Poulcy036' was selected in the spring of 2003 by the inventor as a single plant from the progeny of the aforementioned hybridization.

Asexual reproduction of 'Poulcy036' by rooted cuttings was first done by Mogens N. Olesen in the nursery in Fredensborg, Denmark in July, 2003. This initial and other subsequent asexual propagations conducted in controlled environments have demonstrated that the characteristics of 'Poulcy036' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy036'.

Specifically illustrated in FIG. 1 of the drawings are open flowers viewed from the side an above, a cluster of flowers on the branch, petals and sepals detached showing reproductive flower parts.

Figure 1:
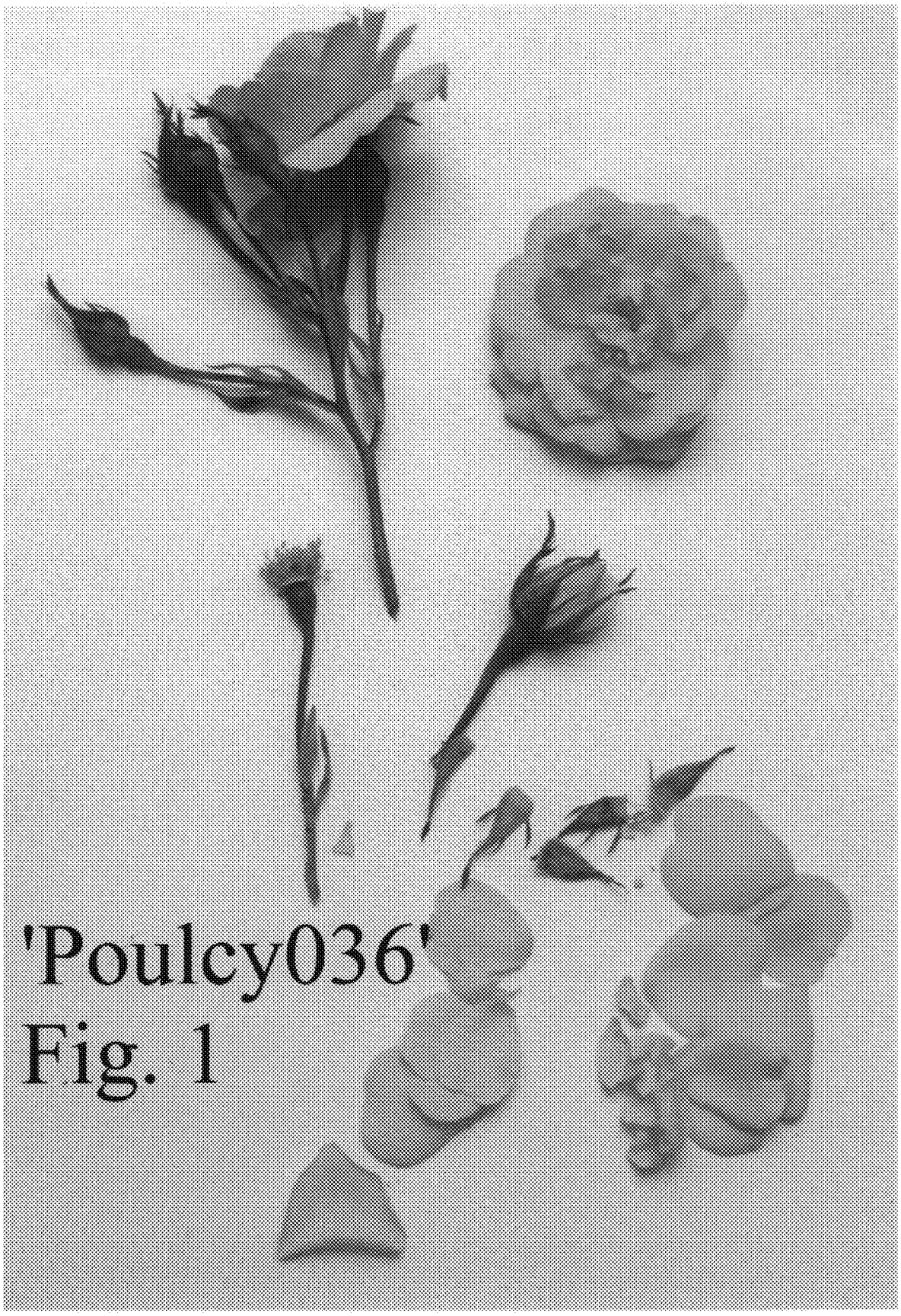
Figure 2:
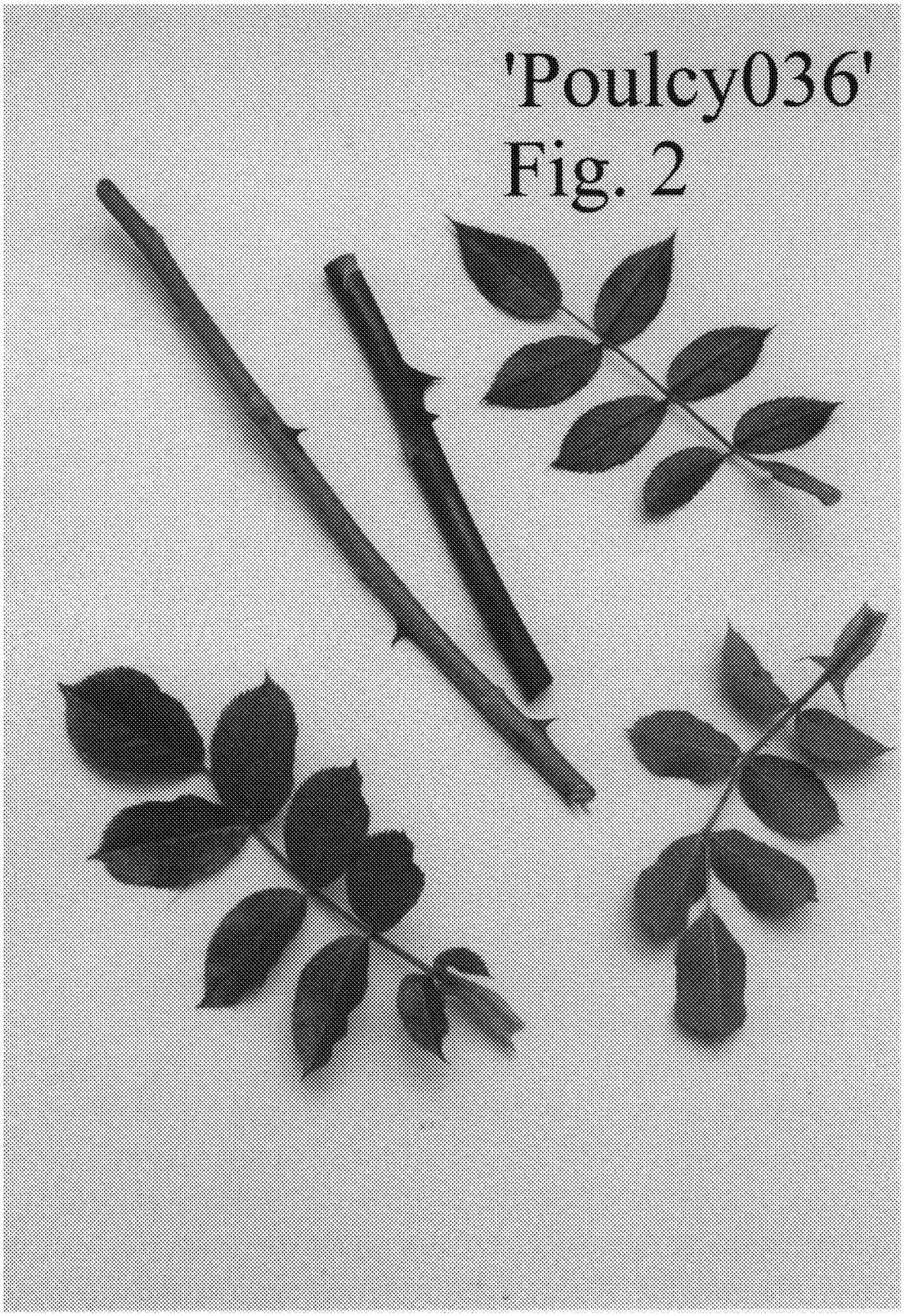

Specifically illustrated in FIG. 2 of the drawings are mature and juvenile leaves and bare stems. Plants shown are 2 years of age.

DETAILED DESCRIPTION OF THE VARIETY

The following is a description of 'Poulcy036', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcy028', U.S. Plant Pat. No. 27,245 are compared to 'Poulcy036' in Chart 1.

CHART 1

| | 'Poulcy036' | 'Poulcy028' |
|---|---|---|
| Petal Count | 25 | 25 |
| Flower Diameter | 55 mm | 55 mm |
| General Tonality of Flower Color | Yellow Group 10A | Yellow Group 13A |

FLOWER AND FLOWER BUD

Blooming habit: Continuous.

Flower bud:

*Size*.—Upon opening, 20 mm in length from base of receptacle to end of bud. Bud diameter is 9 mm.

*Bud form*.—Urceolate.

*Bud color*.—As sepals divide petals are Yellow-Orange Group 16A.

*Sepal inner surface*.—Color: Yellow-Green Group 145B. Surface: Lightly pubescent.

*Sepal outer surface*.—Color: Yellow-Green Group 144A with intonations of Greyed-Red Group 180B. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—25 mm long, 6 mm wide.

*Receptacle*.—Texture: Smooth. Size: 7 mm in height, 5 mm wide. Color: Yellow-Green Group 146C with intonations of Greyed-Purple Group 183C. Shape: Globular.

*Pedicel*.—Surface: Smooth. Length: 30 mm. Diameter: 2 mm on average. Color: Greyed-Red Group 180A and Yellow-Green Group 144A. Strength: Strong.

*Peduncle*.—Length: 5 to 10 cm. Diameter: About 3 mm. Color: Yellow-Green Group 146C with intonations of Greyed-Purple Group 183C. Texture: Smooth.

Flower bud development: Flower buds are borne in clusters of 15 to 17 flower buds on each peduncle.

Flower bloom:

*Fragrance*.—None.

*Duration*.—The blooms have a duration on the plant of approximately 14 days. Petals fall cleanly away from plant after flowers have fully matured.

*Size*.—Flower diameter is 50 mm when open. Flower depth is 20 mm.

*Flower shape*.—Open cup semi double flower, with petals that curve out from the center.

Shape of flower, side view: The upper portion is flat. The lower portion is flattened concave.

Petalage: Under normal conditions, flowers have about 25 petals.

General tonality of flower: Open flowers are Yellow Group 10A.

Petal color:

*Upon opening, outer petals*.—Upper surface: Yellow Group 10A with other intonations of Yellow-Orange Group 16C. Lower surface: Yellow Group 10A splashed with Yellow-Orange Group 19A.

*Upon opening, inner petals*.—Upper surface: Yellow Group 10A with other intonations of Yellow-Orange Group 16C. Lower surface: Yellow Group 10A splashed with Yellow-Orange Group 16B towards the margins.

*Basal petal spots, upon opening*.—Upper surface: Yellow Group 6A. Lower surface: Yellow Group 6A.

*After opening, outer and inner petals*.—Upper surface: Yellow Group 10A with other intonations of Yellow-Orange Group 16C. Lower surface: Yellow Group 10A splashed with Yellow-Orange Group 19A.

*Basal petal spots, after opening*.—Upper surface: Yellow Group 8A. Lower surface: Yellow Group 8A.

Petals:

*Petal reflex*.—None.

*Margin*.—Entire. Occasionally, there is a cleft at the margin. No undulations.

*Shape*.—Broad and elliptic. Apex shape: Emarginate, or rounded. Occasionally with small point at the center. Base shape: Acute.

*Size*.—35 mm (l)×32 mm (w).

*Texture*.—Smooth.

*Thickness*.—Average.

Petaloids:

*Size*.—14 mm (l) by 6 mm (w).

*Quantity*.—About 5.

*Shape*.—Elliptical with an acute base and rounded apex.

*Color*.—Yellow Group 10A with other intonations of Yellow-Orange Group 16C on the upper surface. The lower surface is Yellow Group 10A with other intonations of Yellow-Orange Group 16B.

Reproductive flower parts:

*Pollen*.—None observed.

*Anthers*.—Size: 2 mm in length. Color: Yellow Group 11A. Quantity: 20 on average.

*Filaments*.—Color: Yellow-Orange Group 14C. Length: 3 mm.

*Pistils*.—Length: 4 mm. Quantity: 18 on average.

*Stigmas*.—Color: Greyed-Yellow Group 160D.

*Styles*.—Color: Greyed-Red Group 180D

*Location of stigmas*.—Inferior in location relative to the length of the filaments and the height of the anthers.

*Hips*.—None Observed.

PLANT

Plant growth: Spreading or climbing. Plants are 175 to 200 cm in height, and 100 cm wide.

Stems:

*Color of juvenile growth*.—Yellow-Green Group 144B with strong intonations of Greyed-Purple Group 183A.

*Color of mature growth*.—Yellow-Green Group 146C.

*Length*.—Canes are about 50 cm from the base of the plant to the flowering portion.

*Diameter*.—*About* 9 mm.

*Internodes*.—On mature canes about 45 mm between nodes.

*Surface texture*.—Young wood: Smooth. Older wood: Smooth.

Long prickles:

*Incidence*.—About 3 prickles per 10 cm of stem.

*Size*.—Average length of prickles on mature stems is 6 mm.

*Shape*.—Upper portion is linear. Lower portion is concave.

*Color*.—Juvenile prickles: Greyed-Red Group 179A. Mature prickles: Greyed-Red Group 179A.

Plant foliage:

*Compound leaf*.—140 mm (l)×75 mm (w).

*Quantity*.—2 leaves per 10 cm of stem on average.

*Leaf bearing angle to the stem*.—45 degrees.

*Color of juvenile foliage*.—Upper side: Yellow-Green Group 146A with intonations of Greyed-Purple Group 183A. Lower side: Yellow-Green Group 146B with intonations of Greyed-Purple Group 183A.

*Color of mature foliage*.—Upper side: Yellow-Green Group 146A. Lower side: Yellow-Green Group 146B.

Plant leaves and leaflets:

*Stipules*.—Size: 25 mm long, mm wide. Quantity: 2 per compound leaf. Shape: Linear, slightly broad based with outward extending apices. Margins: Finely serrated. Color: Yellow-Green Group 144B.

*Petiole*.—Length: About 30 mm. Diameter: 2 mm. Upper surface color: Yellow-Green Group 144A. Lower surface color: Yellow-Green Group 144A.

*Rachis*.—Length: About 50 mm. Upper surface color: Yellow-Green Group 144A. Lower surface color: Yellow-Green Group 144A.

*Leaflet*.—Quantity: 7 to 9 leaflets. Margins: Serrated. Size: Terminal leaflets are about 40 mm long, 25 mm wide. Shape: Generally elliptical. Base: Rounded. Apex: Mucronate. Texture: Smooth. Thickness: Average. Arrangement: Odd pinnate. Venation: Reticulate. Glossiness: Moderate to strong gloss.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Climbing rose class named 'Poulcy036', substantially as illustrated and described herein, due to its abundant yellow flowers, disease resistance, and extended period of bloom.

* * * * *

'Poulcy036'

'Poulcy036'